United States Patent [19]

Bacon et al.

[11] Patent Number: 6,110,449
[45] Date of Patent: Aug. 29, 2000

[54] ANHYDROUS ANTIPERSPIRANT CREAM COMPOSITIONS IMPROVED PERFUME LONGEVITY

[75] Inventors: Dennis Ray Bacon, Milford; Judith Ann Hollingshead, Batavia; George Peter Rizzi, Cincinnati; Charles Raymond Tremblay, Mason; Timothy James Welch, Cincinnati, all of Ohio

[73] Assignee: The Procter & Gamble Company, Cincinnati, Ohio

[21] Appl. No.: 09/332,214

[22] Filed: Jun. 14, 1999

[51] Int. Cl.[7] .............................. A61K 7/32; A61K 31/74; A61K 7/00; A61K 7/46; A61L 9/01
[52] U.S. Cl. .............................. 424/65; 422/5; 424/78.03; 424/400; 424/401; 512/1
[58] Field of Search ................................. 424/65, 67, 400, 424/401, 78.03; 422/5; 512/1

[56] References Cited

U.S. PATENT DOCUMENTS

| | | | |
|---|---|---|---|
| 4,803,195 | 2/1989 | Holzner | 512/4 |
| 5,135,747 | 8/1992 | Faryniarz et al. | 424/401 |
| 5,176,903 | 1/1993 | Goldberg et al. | 424/66 |
| 5,635,166 | 6/1997 | Galleguillos et al. | 424/66 |
| 5,672,340 | 9/1997 | Sun et al. | 424/66 |
| 5,861,144 | 1/1999 | Peterson et al. | 424/65 |
| 5,871,718 | 2/1999 | Lucas et al. | 242/65 |
| 5,874,070 | 2/1999 | Trinh et al. | 424/65 |
| 5,942,214 | 8/1999 | Lucas et al. | 424/65 |

FOREIGN PATENT DOCUMENTS

| | | |
|---|---|---|
| 53-41440 | 4/1978 | Japan . |
| 3-284616 | 12/1991 | Japan . |
| 9-315937 | 12/1997 | Japan . |
| 10-120541 | 5/1998 | Japan . |
| WO 98/18439 | 5/1998 | WIPO . |

OTHER PUBLICATIONS

"Cyclodextrins in Foods, Cosmetics, and Toiletries." Hitoshi Hashimoto, 1996; (pp. 483–502).

*Primary Examiner*—Shelley A. Dodson
*Attorney, Agent, or Firm*—Joan B. Tucker; Lucy Elandjian; William J. Winter

[57] ABSTRACT

Disclosed are anhydrous antiperspirant cream compositions that have improved fragrance longevity. These compositions have a penetration force value of from about 75 gram·force to about 500 gram·force and comprise (a) antiperspirant active, and (b) a perfume/cyclodextrin inclusion complex. Also disclosed are packaged anhydrous antiperspirant cream compositions which comprise (a) antiperspirant active; (b) a perfume/cyclodextrin inclusion complex; and (c) a dispensing package containing the composition, wherein the dispensing package comprises (i) a container body having an interior chamber and a dispensing end, and (ii) a perforated dome attached to the dispensing end of the container body and having a plurality of openings extending through the thickness of the perforated dome and covering from about 15% to about 80% of the total surface area of the perforated dome.

34 Claims, No Drawings

ANHYDROUS ANTIPERSPIRANT CREAM COMPOSITIONS IMPROVED PERFUME LONGEVITY

FIELD OF INVENTION

The present invention relates to anhydrous antiperspirant cream compositions which provide improved perfume longevity. In particular, this invention relates to anhydrous antiperspirant cream compositions which contain perfumes that are encapsulated by cyclodextrins to provide for sustained release of the perfumes.

BACKGROUND OF THE INVENTION

There are many types of topical antiperspirant products that are commercially available or otherwise known in the antiperspirant art. Most of these products are formulated as roll-on liquids, creams, emulsions, gels, gel-solids, or other solid stick formulations, and comprise an antiperspirant active and suspending or thickening agent incorporated into a suitable liquid carrier. These products are designed to provide effective perspiration and odor control while also being cosmetically acceptable during and after application onto the axillary area or other areas of the skin. Most of these antiperspirant products contain perfumes which help provide a pleasant fragrance during or after application of the product, or which otherwise help to hide or mask malodors associated with the use of the product.

Perfumes are generally included in antiperspirant products as free perfumes. The free perfumes are often prematurely lost due to various factors including evaporation, especially when the perfume materials are highly volatile perfumes. Therefore, many antiperspirant products are composed mainly of less volatile perfume materials in order to maximize the fragrance character during storage and use of the product. Although the fragrance character of the less volatile perfume materials is more substantive as compared to highly volatile perfumes, both perfume materials can rapidly spread and emit perfume odor impressions upon application of the antiperspirant product on the skin. The rate at which the perfume materials spread and emit fragrance in the surrounding atmosphere generally decreases after application and during use of the product, and this can result in minimal or no consumer perceived perfume odor character after a few hours and sometimes the fragrance duration of these materials is insufficient to help hide or mask perspiration malodors.

In order to extend fragrance character and to ensure greater stability of perfume materials, some antiperspirant products contain perfume inclusion complexes in addition to the free perfumes. The use of complexing agents such as cyclodextrins to stabilize perfume materials and extend fragrance character is well known, and the preparation and use of cyclodextrin inclusion complexes of perfumes and other active materials have been continually described in the art. Cyclodextrins that are typically used in antiperspirant formulations are those cyclodextrin compounds that are soluble in water and insoluble in the antiperspirant matrix to provide for sustained release of the perfume materials until the perfume/cyclodextrin complex comes in contact with water contained in human body fluid such as sweat. The speed of release of the encapsulated perfumes can be influenced by several factors including the particle size of the complex, the amount of water available, and the capacity of antiperspirant product to remain on the skin.

Some antiperspirant products have a tendency to remain on the skin of the user longer than others. Antiperspirant cream products, for example, can have more capacity in contacting the axillary area of the skin and remaining on the axilla as compared to antiperspirant stick products. The antiperspirant creams have a soft texture which allows for easy application and spreadability of the creams. It is believed that the ease of spreading provides more capacity for application of the product and this can result in greater contact between the product and the skin surface.

It has now been found that the fragrance odor impressions of encapsulated perfumes can be improved by incorporating perfume/cyclodextrin inclusion complexes into an anhydrous antiperspirant cream composition. The antiperspirant cream remains on the skin until it is washed-off, and this extended duration of the antiperspirant cream on the skin provides for extended contact of the perfume/cyclodextrin complex with the skin. The antiperspirant cream also provides a stable medium for maintaining the complex on the skin until the complex comes in contact with sweat and the cyclodextrin enclosing the perfume dissolves and releases the perfume. Therefore, the incorporation of perfume/cyclodextrin inclusion complexes in antiperspirant cream formulations provides extended contact of the complexes with the skin and sustained release of perfume materials which can result in fragrance odor impressions for extended periods after application and during use of the antiperspirant cream product. It is believed that these same release profiles are not found in other antiperspirant formulations such as solid sticks and roll-on liquids.

It is therefore an object of the present invention to provide an anhydrous antiperspirant cream composition that has improved fragrance longevity, and further to provide such a composition which contains cyclodextrin inclusion complexes of perfumes. It is a further object of the present invention to provide an anhydrous antiperspirant cream composition that contains perfume/cyclodextrin inclusion complexes that provide for sustained release of the perfumes after application of the composition and upon contact of the complex with human body fluid. It is yet another object of the present invention to provide such a composition that has low visible residue, good dry skin feel, is easy to wash off, provides good efficacy, and that remains stable over extended periods of time.

SUMMARY OF THE INVENTION

The present invention is directed to anhydrous antiperspirant cream compositions that have improved fragrance longevity. These compositions have a penetration force value of from about 75 gram. force to about 500 gram·force and comprise (a) antiperspirant active, and (b) a perfume/cyclodextrin inclusion complex. The anhydrous antiperspirant cream compositions contain less than about 2% by weight of free or added water.

The present invention is also directed to packaged anhydrous antiperspirant cream compositions which comprise (a) antiperspirant active; (b) a perfume/cyclodextrin inclusion complex; and (c) a dispensing package containing the composition, wherein the dispensing package comprises (i) a container body having an interior chamber and a dispensing end, and (ii) a perforated dome attached to the dispensing end of the container body and having a plurality of openings extending through the thickness of the perforated dome and covering from about 15% to about 80% of the total surface area of the perforated dome. The anhydrous antiperspirant cream compositions contained in the dispensing package described hereinabove have a penetration force value of from about 75 gram·force to about 500 gram·force, and contain less than about 2% by weight of free or added water.

The present invention is also directed to a method of treating and preventing perspiration in humans by using the anhydrous antiperspirant cream compositions described herein.

DETAILED DESCRIPTION OF THE INVENTION

The antiperspirant cream compositions of the present invention are liquid dispersions of particulate solids in a continuous water-insoluble or lipophilic phase. These compositions are anhydrous systems which are suitable for use in topical cream applicators, or by other known or otherwise effective means of topically applying a cream to the skin.

The term "anhydrous" as used herein means that the antiperspirant cream composition of the present invention, and the essential or optional components thereof, are substantially free of added or free water. From a formulation standpoint, this means that the antiperspirant cream compositions of the present invention contain less than about 2%, preferably less than about 1%, more preferably less than about 0.5%, most preferably zero percent, by weight of free or added water. The "anhydrous liquid carriers" described herein likewise preferably contain no more than the above described percentages of free or added water.

The term "ambient conditions" as used herein refers to surrounding conditions at about one atmosphere of pressure, at about 50% relative humidity, at about 25° C.

The term "cyclodextrin" (CD) as used herein includes any of the known cyclodextrins such as unsubstituted cyclodextrins containing from six to twelve glucose units, especially alpha-, beta-, gamma-cyclodextrin, and mixtures thereof, and/or their derivatives, and/or mixtures thereof, that are capable of forming inclusion complexes with perfume materials.

The antiperspirant cream compositions of the present invention have a penetration force value of from about 75 gram·force to about 500 gram force, at 27° C., 15% relative humidity, as measured with a TA-XT2 Texture Analyzer, distributed by Texture Technology Corp, Scarsdale, N.J., U.S.A. This value is the force required to move a standardized 45° cone through the product, for a distance of 10 mm, at a rate of 2 mm/second. The angled cone is also available from Texture Technology Corp., as part number TA-15, and has a total cone length of about 24.7 mm, an angled cone length about 18.3 mm, a maximum diameter of the angled surface of the cone of about 15.5 mm. The cone is a smooth, stainless steel construction and weights about 17.8 grams. For use as a conventional antiperspirant cream, or for use in a cream applicator device, the compositions of the present invention preferably have a penetration force value of from about 75 gram·force to about 500 gram·force, more preferably from about 100 gram. force to about 250 gram·force, even more preferably from about 120 gram·force to about 200 gram·force. The antiperspirant cream compositions of the present invention do not include solid antiperspirant stick compositions, which solid sticks have penetration force values substantially greater than about 500 gram·force, typically above about 1000 gram·force.

The anhydrous antiperspirant cream compositions of the present invention can comprise, consist of, or consist essentially of the essential elements and limitations of the present invention described herein, as well as any of the additional or optional ingredients, components, or limitations described herein.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

Perfume/Cyclodextrin Complex Formation

The perfume/cyclodextrin complexes suitable for use in the anhydrous antiperspirant cream compositions of the present invention are formed in any of the ways known in the art or otherwise effective means of forming perfume/cyclodextrin complexes. Typically, the complexes are formed either by mechanically mixing the perfume and the cyclodextrin together in a suitable solvent such as water, or by kneading the ingredients together in the presence of a suitable amount of solvent.

Typically, the perfume/cyclodextrin complexes have a molar ratio of perfume to cyclodextrin of 1:1. However, the molar ratio can be either higher or lower depending on the size of the perfume and the size of the cavity in the particular cyclodextrin compound. The molar ratio can be determined easily by forming a saturated solution of the cyclodextrin and adding the perfume to form the complex. Typically, the complex will precipitate readily. If not, the complex can usually be precipitated by the addition of electrolyte, change of pH, cooling, and so forth. The complex can then be analyzed to determine the molar ratio of perfume to cyclodextrin.

As stated hereinbefore, typical complexes are formed by bringing together one molecule of the perfume and one molecule of cyclodextrin. However, the complexes can also be formed between one molecule of perfume and two molecules of cyclodextrin when the perfume material is large and contains two portions that can fit in the cyclodextrin. Preferably, the complexes are formed using mixtures of cyclodextrins since some perfumes are usually mixtures of materials that vary widely in size. It is preferred that at least a majority of the cyclodextrin mixture be alpha-, beta-, and/or gamma-cyclodextrin, more preferably beta-cyclodextrin.

Processes for the production of cyclodextrins and/or for forming perfume/cyclodextrin complexes are described in U.S. Pat. No. , 3,812,011, issued to Okada et al. on May 21, 1974; U.S. Pat. No. 4,317,881, issued to Yagi et al. on Mar. 2, 1982; U.S. Pat. No. 4,418,144, issued to Okada et al. on Nov. 29, 1983; U.S. Pat. No. 4,378,923, issued to Ammeraal on Apr. 19, 1988; Atwood, J. L., J. E. D. Davis & D. D. MacNichol, (Ed.): *Inclusion Compounds*, Vol. III, Academic Press (1984), especially Chapter 11; and Atwood, J. L. and J. E. D. Davis (Ed.): *Proceedings of the Second International Symposiums of Cyclodextrins* Tokyo, Japan, (July, 1984); all of which descriptions are incorporated by reference herein. Materials obtained by any of these variations are acceptable for the purposes of this invention. It is also acceptable to initially isolate the inclusion complexes directly from the reaction mixture by crystallization.

Continuous processes for the preparation of cyclodextrins and/or perfume/cyclodextrin complexes usually involves the use of super-saturated solutions, and/or kneading, and/or temperature manipulation, e.g., heating and then either cooling, freeze-drying, and so forth. The complexes may be dried or not depending on the next step in the process for making the desired antiperspirant cream composition. Generally, the fewest process steps are used to avoid loss of the perfume materials.

Complex Particle Size

The particle size of the perfume/cyclodextrin complexes defined herein is selected according to the desired anhydrous antiperspirant cream formulation. The particle size typically range from about 0.001 μm to about 12 μm, preferably from about 0.01 μm to about 8 μm, more preferably from about 0.05 μm to about 5 μm. It is preferred that at least an effective amount of the perfume be in complexes having the particle size range defined above. Preferably, at least about 75%, more preferably at least about 80%, even more preferably at least about 90% of the complex that is present have the particle sizes defined herein. It is most preferred that essentially all of the complex has the particle sizes defined herein.

As used herein, the particle size refers to the largest dimension of the particles and to the ultimate (or primary particles). The size of these primary particles can be directly determined with optical or scanning electron microscopes. The slides must be carefully prepared so that each contains a representative sample of the bulk cyclodextrin complexes. The particle sizes can also be measured by any of the other well-known methods, e.g., wet sieving, sedimentation, light scattering, and the like. A convenient instrument that can be used to determine the particle size distribution of dry complex powder directly (without having to make a liquid suspension or dispersion) is the Malvern Particle and Droplet Sizer, Model 2600C, sold by Malvern Instruments, Inc., located in Southborough Mass. Some caution should be observed in that some of the dry particles may remain agglomerated. The presence of agglomerates can be further determined by microscopic analysis. Some other suitable methods for particle size analysis are described in the article "Selecting a particle size analyzer: Factors to consider," by Michael Pohl, published in Powder and Bulk Engineering, Volume 4 (1990), pp.26–29, which description is incorporated by reference herein. It is recognized that the very small complex particles of the present invention can readily aggregate to form loose agglomerates that are easily broken apart by either some mechanical action or by the action of water. Accordingly, particles should be measured after they are broken apart, e.g., by agitation or sonication. The method, of course, should be selected to accommodate the particle size and maintain the integrity of the complex particles, with iterative measurements being made if the original method selected proves to be inappropriate.

Cyclodextrins

The anhydrous antiperspirant cream compositions of the present invention comprise cyclodextrins that are capable of forming inclusion complexes with the perfume materials described hereinafter. The cyclodextrin can be used individually or as a mixture of cyclodextrins, provided that the cyclodextrin is capable of encapsulating the perfumes and provide for sustained release of the perfume materials.

The cyclodextrins for use in the anhydrous antiperspirant cream compositions of the present invention include those cyclic polysaccharide compounds containing from about 6 to about 12 glucose units. The specific coupling and conformation of the glucose units enable the cyclodextrin to form a rigid, conical molecular structure that has a hollow interior or cavity. In other words, the cyclodextrins can form clathrate compounds which can be characterized as molecular compounds that are formed by the inclusion of molecules such as fragrance molecules in cavities of the crystal lattice of the cyclodextrin compound.

The cyclodextrins for use herein are chemically stable water-soluble compounds that can be used in crystal, powder, or granule form for encapsulation with the perfumes. Water-soluble cyclodextrin derivatives are also highly desirable. The cyclodextrin inclusion complexes of the perfumes (perfume/cyclodextrin, or perfume/CD complexes), as described herein, are stable throughout the mixing of the complex with the remainder of the composition, and during and after application of the composition onto the axillary area or other areas of the skin.

The concentration of the perfume/cyclodextrin inclusion complex may vary with each selected antiperspirant cream formulation, but such concentrations will generally range from about 0.05% to about 20%, preferably from about 0.1% to about 10%, more preferably from about 2% to about 8%, by weight of the composition.

Cyclodextrins for use herein to form inclusion complexes with the perfumes include any of the known cyclodextrins such as alpha-, beta-, gamma-cyclodextrins, and mixtures thereof, and/or their derivatives, and/or mixtures thereof. Beta-cyclodextrin is most preferred. Nonlimiting examples of suitable cyclodextrin derivatives for use to form the perfume inclusion complexes include methyl-b-CD, hydroxyethyl-b-CD, and hydroxypropyl-b-CD of different degrees of substitution (DS). Other examples of suitable cyclodextrin derivatives are disclosed in U.S. Pat. No. 3,426,011, issued to Parmerter et al. on Feb. 4, 1969; U.S. Pat. Nos. 3,453,257, 3,453,258, 3,453,259, and 3,453,260, all issued to Parmerter et al. on Jul. 1, 1969; U.S. Pat. No. 3,459,731, issued to Gramera et al. on Aug. 5, 1969; U.S. Pat. No. 3,553,191, issued to Parmerter et al. on Jan. 5, 1971; U.S. Pat. No. 3,565,887, issued to Parmerter et al. on Feb. 23, 1971; U.S. Pat. No. 4,535,152, issued to Szejtli et al. on Aug. 13, 1985; U.S. Pat. No. 4,616,008, issued to Hirai et al. on Oct. 7, 1986; U.S. Pat. No. 4,638,058, issued to Brandt et al. on Jan. 20, 1987; U.S. Pat. No. 4,746,734, issued to Tsuchiyama et al. on May 24, 1988; and U.S. Pat. No. 4,678,598, issued to Ogino et al. on Jul. 7, 1987; all of which disclosures are incorporated by reference herein. Alpha-, beta-, gamma-cyclodextrins and/or their derivatives can be obtained from, among others, Cerestar USA, Inc., located in Hammond, Ind.; Wacker Chemicals (USA), Inc., located in New Canaan, Conn.; Aldrich Chemical Company located in Milwaukee, Wis.; and Chinoin Pharmaceutical Works located in Budapest, Hungary.

Other suitable cyclodextrin materials for use herein include those individual cyclodextrins linked together, e.g., using multifunctional agents, to form oligomers, or other polymers. Nonlimiting examples of such materials include cyclodextrin polymers that are formed by crosslinking a cyclodextrin monomer with an aromatic, aliphatic, or cycloaliphatic polyfunctional crosslinking agent. Suitable cyclodextrin monomer materials include, but are not limited to, alpha-cyclodextrin, beta-cyclodextrin, gamma-cyclodextrin, substituted alpha-cyclodextrin, substituted beta-cyclodextrin, and substituted gamma-cyclodextrin. Branched cyclodextrin monomer materials are also suitable for use herein. Specific examples of suitable polyfunctional crosslinking agents include, but are not limited to, diisocyanates, polyisocyanates, dihalohydrocarbons, and dihaloacetylhydrocarbons. Other suitable polyfunctional crosslinking agents can include asymmetric crosslinking agents containing different linking functionalities such as isocyanate, halo, or haloacetyl, an example of which include 4-isocyanatobenzoyl chloride. Specific examples of cyclodextrin polymers that are suitable for use herein include, but are not limited to, beta-cyclodextrin crosslinked by epichlorohydrin and ethyleneglycolbis (epoxypropyl ether); and alpha-, beta-, or gamma-cyclodextrin crosslinked by a polyisocyanate or dihalohydrocarbon polyfunctional crosslinking agent. Other polymeric forms are also suitable for use herein, such as carboxylic acid containing polymer-cyclodextrin conjugates which may be prepared by conjugating a suitable carboxylic acid containing polymer to a cyclodextrin monomer using any method well known in the art for preparing cyclodextrin polymers.

Mixtures of cyclodextrins are also preferred to provide perfume/cyclodextrin inclusion complexes. Mixtures of cyclodextrin can conveniently be obtained by using intermediate products from known processes for the preparation of cyclodextrins, examples of which include those processes described in U.S. Pat. No. 3,425,910 issued to Armbruster et al. on Nov. 29, 1983; and U.S. Pat. No. 4,738,923, issued to Ammeraal on Apr. 19, 1988; both descriptions of which are incorporated by reference herein. Preferably, at least a major portion of the cyclodextrin mixtures is alpha-cyclodextrin, beta-cyclodextrin, and/or gamma-cyclodextrin, more preferably beta-cyclodextrin. Some commercial examples of cyclodextrin mixtures are available from Ensuiko Sugar Refining Company located in Yokohama, Japan.

Fragrance Materials

The anhydrous antiperspirant cream compositions of the present invention comprise encapsulated perfume materials to improve the fragrance odor of the composition, and to provide extended fragrance odor impressions. The encapsulated perfumes are sustained in the compositions until they are preferably released by contact between the perfume/cyclodextrin complex and water contained in human body fluid such as sweat.

The concentration of the perfume materials is preferably sufficient to provide olfactory detection of the encapsulated perfume upon release of the perfume from the composition. An individual perfume or mixtures of these materials may be used to form the perfume/cyclodextrin complexes described herein. Typically, the perfumes are included in the complex as a mixture of perfumes at a total perfume concentration ranging from about 0.1% to about 30%, preferably from about 1% to about 20%, more preferably from about 5% to about 15%, by weight of the complex.

The anhydrous antiperspirant cream compositions of the present invention comprise the perfume/cyclodextrin complex. The compositions may optionally comprise a combination of the complex and free perfume. Preferably, the compositions contain both free perfume materials and complexed perfumes. Thus, by adjusting the levels of free perfume and the perfume/cyclodextrin complex it is possible to provide a wide range of unique perfume profiles in terms of perfume release and/or perfume character.

The optional free perfume for use in the anhydrous antiperspirant cream compositions include one or more individual perfume chemicals, provided that the optional free perfume can emit a detectable perfume odor. Concentrations of the optional free perfume preferably range from about 0.10% to about 10%, more preferably from about 0.5% to about 3%, by weight of the compositions. The free perfume is very useful in imparting an initial perfume odor that can serve as a signal that the antiperspirant cream product is effective.

The perfume materials for use in the anhydrous antiperspirant cream compositions of the present invention include any known perfumes in the art or any otherwise effective perfume materials. Many of the perfumes described herein, along with their odor characters and their physical and chemical properties such as boiling point and molecular weights, are disclosed in "Perfume and Flavor Chemicals (Aroma Chemicals)," S. Arctander, published by the author, 1969, incorporated herein by reference.

Nonlimiting examples of suitable perfumes for use herein include anethole, benzaldehyde, decyl aldehyde, amyl acetate, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, helional, cis-3-hexenol, cis-3-hexenyl acetate, dipropylene glycol, diethyl phthalate, phenyl ethyl acetate, dihydrocitronellal, d-limonene, linalool, linalool oxide, tetra-hydro linalool, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, prenyl acetate, manjantol, ambrettolide, ambroxan, cetelox, phenyl ethyl alcohol, phenyl acetaldehyde, alpha-pinene, beta-pinene, gamma-terpinene, alpha-terpineol, beta-terpineol, terpinyl acetate, vertenex (para-tertiary-butyl cyclohexyl acetate), alpha damascone, damascone beta, undecalactone, undecylenic aldehyde, amyl cinnamic aldehyde, iso-amyl salicylate, beta-caryophyllene, cedrene, cinnamic alcohol, coumarin, cymal, dimethyl benzyl carbinyl acetate, dimethyl benzyl carbinol, ethyl vanillin, eugenol, iso-eugenol, dihydro-norcyclopentadienyl acetate, dihydro-nor-cyclopentadienyl propionate, heliotropine, cyclohexyl salicylate, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, veratraldehyde, 2-methyl-3-(para tert butylphenyl)-propionaldehyde, benzophenone, benzyl salicylate, ethylene brassylate, galaxolide (1,3,4,6,7,8-Hexahydro-4,6,6,7,8,8-hexamethyl-cyclopenta-gamma-2-benzopyran), hexyl cinnamic aldehyde, lyral (4-(4-hydroxy-4-methylpentyl)-3-cyclohexene- 10-carboxaldehyde), methyl cedrylone, dihydro isojasmonate, methyl dihydro jasmonate, methyl-beta-naphthyl ketone, gamma decalactone, musk indanone, musk ketone, musk tibetene, phenylethyl phenyl acetate, cyfleural S6MC, PE isobutyrate, PE propionate, tripal, LRG 201, ligustral, and mixtures thereof.

Other suitable perfumes for use herein include any known natural oil perfume material in the art. Nonlimiting examples of natural oils include terpenes; patchouli oils; french crop oils; citrus oils; clove derivatives; gums, mosses, and resins; and general natural oils. Specific examples of terpenes include, but are not limited to, orange terpenes, lemon terpenes, clementine terpenes, cedarwood terpenes, grapefruit terpenes, grapefruit terpenes distilled, and mixtures thereof. Specific examples of patchouli oils include, but are not limited to, patchouli decolorized, patchouli oil md, patchouli enhancer PG 67002, patchouli B50010 coeur (798304), patchouli booster AN113418, patchouli oil I.F.indo A, and mixtures thereof. Specific examples of french crop oils include, but are not limited to, lavandin, lavandin grosso, spike lavender, clary sage, and mixtures thereof. Specific examples of citrus oils include, but are not limited to, Italian orange phase oil, cold pressed orange oil, orange oil tarocco 5X (10982), lemon oil, lemon c.p., tangerine distilled oil, tangerine oil, and mixtures thereof. Specific examples of clove derivatives include, but are not limited to, eugenol, iso eugenol, iso eugenol acetate, clove stem oil, clove bud oil, and mixtures thereof. Specific examples of gums, mosses, and resins include, but are not limited to, styrax resin 50% in DPG, olibanium resinoid 80%, peru balsam, labdanum clair, styrax white, oakmoss 25%, geranium S, and mixtures thereof. Specific examples of general natural oils include, but are not limited to, citronella, petitgrain, elemi oil, galbanum 50%, ylang ylang, rosemary, menthol, menthol natural, caraway, cananga, nutmeg, coriander, cassia oil, celery seed oil, and mixtures thereof.

Other suitable perfumes for use herein include specialty perfumes which contain a combination of perfume materials. Nonlimiting examples of specialty perfumes include Base Jasmin AN101970 available from Noville, Inc. located in South Hackensack, N.J., U.S.A.; Kir Base #9741 available from BBA-Chem, Corp. located in Montvale, N.J., U.S.A.; Cassis Base 345-B available from Firmenich, Inc located in Princeton, N.J., U.S.A; VL Base PG available from Givaudan, Corp. located in Teaneck, N.J., U.S.A; Alvanone Extra available from International Flavors and Fragrances, Inc. located in New York, N.Y., U.S.A.; Irisia Base available from Firmenich, Inc located in Princeton, N.J., U.S.A.; Irival available from International Flavors and Fragrances, Inc. located in New York, N.Y., U.S.A.; Iritone available from International Flavors and Fragrances, Inc. located in New York, N.Y., U.S.A; and mixtures thereof.

Other nonlimiting examples of suitable perfume materials are disclosed in U.S. Pat. No. 4,145,184, issued to Brain and Cummins on Mar. 20, 1979; U.S. Pat. No. 4,209,417, issued to Whyte on Jun. 24, 1980; U.S. Pat. No. 4,515,705, issued to Moeddel on May 7, 1985; and U.S. Pat. No. 4,152,272, issued 4,152,272, issued to Young on May 1, 1979; all of which disclosures are incorporated by reference herein.

Embodiments of Perfume/Cyclodextrin Complexes

The anhydrous antiperspirant cream compositions of the present invention include those embodiments which contain a perfume/cyclodextrin complex comprising one or more highly volatile perfume materials that have a boiling point of less than or equal to 250° C. It is believed that highly volatile perfume materials can provide improved fragrance aesthetics such as fresh and clean odor impressions, and it is desirable that these perfume materials be included in the compositions via perfume/cyclodextrin complexes. Preferably, at least about 90%, more preferably at least about 95%, even more preferably at least about 98%, most preferably essentially all of the perfumes present in these perfume/cyclodextrin complexes are highly volatile perfume materials.

Nonlimiting examples of preferred highly volatile perfume materials that have a boiling point less than or equal to 250° C. include anethole, benzaldehyde, decyl aldehyde, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiary-butyl cyclohexyl acetate), gamma-methyl ionone, undecalactone, undecylenic aldehyde, alpha-damascone, beta-damascone, amyl acetate, lemon oil, orange oil, and mixtures thereof.

Preferably, these perfume/cyclodextrin complexes are substantially free of encapsulated perfumes that have a boiling point of greater than 250° C. In this context, the term "substantially free" means that these perfume/cyclodextrin complexes preferably contain less than an effective amount of such encapsulated perfume materials to provide olfactory detection of fragrance odor impressions. Preferably, less than about 10%, more preferably less than about 8%, even more preferably less than about 5%, most preferably zero percent, of the perfumes present in these perfume/cyclodextrin complexes are perfume materials that have a boiling point of greater than 250° C.

Antiperspirant Active

The anhydrous antiperspirant cream compositions of the present invention comprise a particulate antiperspirant active suitable for application to human skin. Suitable actives for use in the compositions are those which remain substantially unsolubilized as dispersed solid particulates in an anhydrous or substantially anhydrous system. The concentration of active in the compositions should be sufficient to provide the desired odor and wetness control from the antiperspirant cream formulation selected.

The anhydrous antiperspirant cream compositions of the present invention preferably comprise the antiperspirant active particles at concentrations of from about 0.5% to about 35%, more preferably from about 10% to about 30%, by weight of the compositions. These weight percentages are calculated on an anhydrous metal salt basis exclusive of water and any complexing agents such as glycine, glycine salts, or other complexing agents. The antiperspirant active particles as formulated in the compositions are in the form of dispersed solid particles having a preferred average particle size or diameter of from about 1 μm to about 100 μm, more preferably from about 1 μm to about 50 μm.

The antiperspirant actives for use in the anhydrous antiperspirant cream compositions of the present invention include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum hydroxyhalides, zirconyl oxyhalides, zirconyl hydroxyhalides, and mixtures thereof.

Preferred aluminum salts for use in the anhydrous antiperspirant cream compositions include those which conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorhydroxides referred to as "5/6 basic chlorhydroxide", wherein a=5, and "2/3 basic chlorhydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980; all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the anhydrous antiperspirant cream compositions include those which conform to the formula:

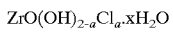

$$ZrO(OH)_{2-a}Cl_a \cdot xH_2O$$

wherein a is any number having a value of from about 0 to about 2; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorhydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No. 4,120,948, Shelton, issued Oct. 17, 1978; all of which are incorporated herein by reference.

The anhydrous antiperspirant cream compositions of the present invention can also be formulated to comprise other dispersed solids or other materials in addition to or in place of the antiperspirant active particles. Such other dispersed solids or other materials include any material known or otherwise suitable for topical application to human skin. The anhydrous antiperspirant cream compositions can also be formulated as cosmetic creams which contain no antiperspirant or other active material, particulate or otherwise.

Suspending or Thickening Agent

The anhydrous antiperspirant cream compositions of the present invention preferably comprise a suspending or thickening agent to help provide the compositions with the desired viscosity or product hardness, or to otherwise help suspend any dispersed solids or liquids within the compositions. Suitable suspending or thickening agents include any material known or otherwise effective in providing suspending or thickening properties to the compositions, or which otherwise provide structure to the final product form. These suspending or thickening agents include gelling agents, and polymeric or nonpolymeric or inorganic thickening or viscosifying agents. Such materials will most typically include organic solids, silicone solids, crystalline or other gellants, inorganic particulates such as clays or silicas, or combinations thereof.

The concentration of the suspending or thickening agent in the compositions may vary with each selected antiperspirant cream formulation, especially with each selected anhydrous liquid carrier of the formulation, but such concentrations will generally range from about 0.1% to about 20%, preferably from about 1% to about 15%, more preferably from about 3% to about 12%, by weight of the compositions.

Suitable gelling agents for use as a suspending or thickening agent in the compositions are solids under ambient conditions. These solid gelling agents preferably have a melting point of from 60° C. to about 140° C., preferably from about 60° C. to about 120° C., more preferably from about 70° C. to about 110° C.

The gelling agents for use in the anhydrous antiperspirant cream compositions are those which can melt and form a homogenous liquid or homogenous liquid dispersion with the selected anhydrous liquid carrier, and at the selected gellant and liquid carrier concentrations, at a processing temperature of from about 28° C. to about 125° C. The melted gelling agent is typically dispersed throughout the selected liquid carrier to thus form a homogenous liquid. The homogenous liquid, and other essential and optional ingredients, are preferably combined in accordance with the manufacturing method herein, placed in a suitable package as a flowable homogenous liquid, and then allowed to solidify and form the desired gellant matrix within the composition as the temperature returns to ambient temperatures and drops to below the solidification point of the selected gelling agent.

Nonlimiting examples of suitable gelling agents include, but are not limited to, fatty alcohols, esters of fatty alcohols, fatty acids, amides of fatty acids, esters or ethers of fatty acids including triglycerides, ethoxylated fatty alcohols, ethoxylated fatty acids, corresponding salts thereof, combinations thereof, and other gellants known or otherwise effective in providing the desired product form, viscosity, and hardness. All such gelling agents preferably have a fatty alkyl moiety having from about 14 to about 60 carbon atoms, more preferably from about 20 to about 40 carbon atoms, and which may be saturated or unsaturated, substituted or unsubstituted, branched or linear or cyclic. Preferred fatty alkyl moieties are saturated, more preferably saturated and unsubstituted.

The term "substituted" as used herein refers to chemical moieties known or otherwise effective for attachment to gelling agents or other compounds. Such substituents include those listed and described in C. Hansch and A. Leo, *Substituent Constants for Correlation Analysis in Chemistry and Biology* (1979), which listing and description are incorporated herein by reference. Examples of such substituents include, but are not limited to, alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

The term "corresponding salts" as used herein refers to cationic salts formed at any acidic (e.g., carboxyl) group, or anionic salts formed at any basic (e.g., amino) group, either of which are suitable for topical application to human skin. Many such salts are known in the art, examples of which are described in World Patent Publication 87/05297, Johnston et al., published Sep. 11, 1987, which description is incorporated herein by reference.

Nonlimiting examples of esters of fatty alcohols suitable for use as gelling agents include tri-isostearyl citrate, tristearylcitrate, stearyl octanoate, stearyl heptanoate, trilaurylcitrate, and mixtures thereof.

Suitable fatty alcohol gelling agents may be used in the compositions at concentrations preferably ranging from about 0.1% to about 8%, more preferably from about 3% to about 8%, even more preferably from about 3% to about 6%, by weight of the compositions. The fatty alcohol gelling agents are also preferably saturated, unsubstituted, monohydric alcohols or combinations thereof, which have a melting point preferably less than about 110° C. Specific examples of fatty alcohol gelling agents for use in the anhydrous antiperspirant cream compositions that are commercially available include, but are not limited to, Unilin 550, Unilin 700, Unilin 425, Unilin 400, Unilin 350, and Unilin 325, all supplied by Petrolite.

Suitable ethoxylated gelling agents include, but are not limited to, Unithox 325, Unithox 400, Unithox 450, Unithox 480, Unithox 520, Unithox 550, Unithox 720, and Unithox 750, all of which are available from Petrolite.

Suitable fatty acid esters for use as gelling agents include ester waxes, monoglycerides, diglycerides, triglycerides, and combinations thereof. Preferred are the glyceride esters. Nonlimiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Preferred are glyceryl tribehenate and other triglycerides, wherein at least about 75%, preferably about 100%, of the esterified fatty acid moieties of said other triglycerides each have from about 18 to about 36 carbon atoms, and wherein the molar ratio of glyceryl tribehenate to said other triglycerides is from about 20:1 to about 1:1, preferably from about 10:1 to about 3:1, more preferably from about 6:1 to about 4:1. The esterified fatty acid moieties may be saturated or unsaturated, substituted or unsubstituted, linear or branched, but are preferably linear, saturated, unsubstituted ester moieties derived from fatty acid materials having from about 18 to about 36 carbon atoms. The triglyceride gelling agent preferably has a preferred melting point of less than about 110° C. Preferred concentrations of the triglyceride gelling agents in the anhydrous antiperspirant cream composition range from about 4% to about 20%, more preferably from about 4% to about 10%, by weight of the composition. Specific examples of preferred triglyceride gelling agents include, but are not limited to, tristearin, tribehenate, behenyl palmityl, behenyl triglyceride, palmityl stearyl, palmityl triglyceride, hydrogenated vegetable oil, hydrogenated rape seed oil, castor wax, fish oils, tripalmitin, Syncrowax HRC and Syncrowax HGL-C (Syncrowax is available from Croda, Inc.). Other suitable glycerides include, but are not limited to, glyceryl stearate and glyceryl distearate.

Suitable amide gelling agents include monoamide gellants, diamide gellants, triamide gellants, and combinations thereof, nonlimiting examples of which include cocoamide MEA (monoethanolamide), stearamide, oleamide, oleamide MEA, tallow amide monoethanolamide, and the n-acyl amino acid amide derivatives such as n-acyl amino acid amides, n-acyl amino acid esters prepared from glutamic acid, lysine, glutamine, apartic acid, and combinations thereof. Other suitable amide gelling agents are described in U.S. Pat. No. 5,429,816 (Hofrichter et al.) and U.S. Pat. No. 5,840,287 (Guskey et al.), which descriptions are incorporated by reference herein.

Suitable fatty acid gelling agents include, but are not limited to, 12-hydroxystearic acid and derivatives thereof, behenic acid, eurcic acid, stearic acid, C20 to C40 fatty acids, and related gellants, some preferred examples of which are disclosed in U.S. Pat. No. 5,429,816, issued to Hofrichter et al. on Jul. 4, 1995; and U.S. Pat. No. 5,552,136, issued to Motley on Sep. 3, 1996; both disclosures of which are incorporated by reference herein. Some commercial examples of fatty acid gelling agents include, but are not limited to, Unicid 400, available from Petrolite.

Preferred gelling agents for use in the anhydrous antiperspirant cream compositions include coconut monoethanolamide, glyceryl tribehenate, C18-36 triglyceride, hydrogenated rapeseed oil, C20 to C40 alcohols, C20 to C40 pareth-3, and combinations thereof. Concentration of coconut monoethanolamide in the composition preferably ranges from about 5% to about 20%, more preferably from about 5% to about 15%, by weight of the composition. Coconut monoethanolamide is especially preferred when used in compositions containing a volatile silicone solvent, especially volatile cyclopentasiloxane, and in compositions containing a combination of a volatile silicone carrier and a nonvolatile silicone (e.g., nonvolatile dimethicones) or a nonvolatile organic carrier.

Glyceryl tribehenate and hydrogenated rapeseed oil are also preferred gelling agents when used in gellant systems containing C20 to C40 fatty alcohols and/or C20 to C40 pareth-3, wherein the weight ratio of glyceryl tribehenate or hydrogenated rapeseed oil to C20 to C40 fatty alcohols and/or C20 to C40 pareth-3 is from about 20:1 to about 1:1, preferably from about 10:1 to about 3:1. These gelling agents are especially preferred when used in compositions containing volatile silicone carrier, especially volatile cyclopentasiloxane, and in compositions containing a combination of a volatile silicone carrier and a nonvolatile silicone (e.g., nonvolatile dimethicones) or a nonvolatile organic carrier.

Many gelling agents are suitable for use in the anhydrous antiperspirant cream composition of the present invention, provided that the gelling agent can be formulated to form a gellant matrix within the composition. In particular, the selected gelling agent should be combined with an appropriate anhydrous liquid carrier and formulated into the composition so as to form a gellant matrix, wherein the size of the gellant particles in the matrix are minimized.

The gelling agent in the composition preferably has an average particle size within the gellant matrix of less than about 10 $\mu$m, more preferably from about 0.1 $\mu$m to about 5 $\mu$m, even more preferably from about 1 $\mu$m to about 4 $\mu$m. The smaller particles form an improved gellant matrix within which the dispersed particulate antiperspirant active and perfume/cyclodextrin complex are physically held in place over extended periods, and within which the anhydrous liquid carrier component of the composition is held with minimal syneresis during storage, transport and extrusion through a perforated dome.

Other suitable suspending or thickening agents for use in the anhydrous antiperspirant cream compositions include particulate suspending or thickening agents such as clays and colloidal pyrogenic silica pigments. Other known or otherwise effective particulate suspending or thickening agents can likewise be used in the anhydrous antiperspirant cream compositions. Concentrations of the particulate thickening agents preferably range from about 0.001% to about 15%, more preferably from about 1% to about 15%, even more preferably from about 1% to about 8%, by weight of the composition. Colloidal pyrogenic silica pigments are preferred, a common example of which includes Cab-O-Sil®, a submicroscopic particulated pyrogenic silica.

Suitable clay suspending or thickening agents include montmorillonite clays, examples of which include bentonites, hectorites, and colloidal magnesium aluminum silicates. These and other suitable clay suspending agents are preferably hydrophobically treated, and when so treated will generally be used in combination with a clay activator. Non-limiting examples of suitable clay activators include propylene carbonate, ethanol, and combinations thereof. The amount of clay activator will typically range from about 25% to about 75% by weight of the clay, more typically from about 40% to about 60%, by weight of the clay.

Anhydrous Liquid Carrier

The anhydrous antiperspirant cream compositions of the present invention comprise an anhydrous liquid carrier wherein the anhydrous liquid carrier comprises one or more liquid carriers each or collectively having a solubility parameter of from about 3 $(cal/cm^3)^{0.5}$ to about 13 $(cal/cm^3)^{0.5}$, preferably from about 5 $(cal/cm^3)^{0.5}$ to about 11 $(cal/cm^3)^{0.5}$, more preferably from to about 9 $(cal/cm^3)^{0.5}$. The term "liquid carrier" and "carrier" are used interchangeably herein, and refer to the anhydrous liquid carrier component of the composition, which forms a homogenous liquid with the selected suspending or thickening agents as described herein.

Solubility parameters for selected liquid carriers or other materials, and means for determining such parameters, are well known in the antiperspirant art. A description of solubility parameters and means for determining them are described by C. D. Vaughan, "Solubility: Effects in Product, Package, Penetration and Preservation" 103 Cosmetics and Toiletries 47–69, Oct. 1988; and C. D. Vaughan, "Using Solubility Parameters in Cosmetics Formulation", 36 J. Soc. Cosmetic Chemists 319–333, September/October, 1985; which descriptions are incorporated herein by reference.

Concentrations of the anhydrous liquid carrier in the compositions will vary with the type of liquid carrier selected, the type of suspending or thickening agent used in combination with the liquid carrier, and the solubility of the selected suspending or thickening agent in the selected carrier, and so forth. Preferred concentrations of the anhydrous liquid carrier ranges from about 10% to about 90%, preferably from about 20% to about 80%, more preferably from about 35% to about 70%, by weight of the compositions.

The anhydrous liquid carrier comprises one or more liquid carriers suitable for topical application to human skin, which carrier or combination of liquid carriers are liquid under ambient conditions. These liquid carriers may be organic or silicone-containing, volatile or nonvolatile, polar or nonpolar, provided that the carrier can form a homogenous liquid or homogenous liquid dispersion with the selected suspending or thickening agent at the selected suspending or thickening agent concentration at a temperature of from about 28° C. to about 125° C. The anhydrous liquid carrier preferably has a low viscosity to provide for improved spreading performance on the skin, more preferably less than about 50 cs (centistokes), even more preferably less than about 10 cs.

The anhydrous liquid carrier preferably comprises one or more volatile carriers, optionally in combination with a nonvolatile carrier. In this context, the term "volatile" refers to carriers having a measurable vapor pressure under ambient conditions of at least 0.01 mm of Hg, and the term "nonvolatile" refers to carriers which do not have a measurable vapor pressure or which have a vapor pressure of less than 0.01 mm of Hg under ambient conditions.

Preferred volatile liquid carriers are the volatile silicone carriers, which includes cyclic, linear or branched chain volatile silicones. Nonlimiting examples of suitable volatile silicones are described in Todd et al., "Volatile Silicone Fluids for Cosmetics", Cosmetics and Toiletries, 91:27–32 (1976), which descriptions are incorporated herein by reference. Preferred volatile silicone materials are those having from about 3 to about 7, more preferably from about 4 to about 5, silicone atoms. Cyclic silicones are preferred.

Suitable cyclic silicones for use in the anhydrous antiperspirant cream compositions include those volatile silicones which conform to the formula:

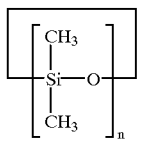

wherein n is from about 3 to about 7, preferably from about 4 to about 5, most preferably 5. These cyclic silicone materials will generally have viscosity values of less than about 10 cs at 25° C.

Suitable linear silicones for use in the anhydrous antiperspirant cream compositions include those volatile linear silicones which conform to the formula:

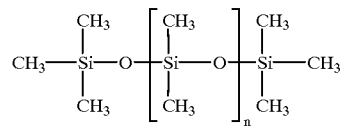

wherein n is from 0 to about 7, preferably from about 2 to about 3. These linear silicone materials will generally have viscosity values of less than about 5 cs at 25° C.

Specific examples of volatile silicone carriers suitable for use in the anhydrous antiperspirant cream compositions include, but are not limited to, Silicone Fluids SF-1202 and SF-1173 (commercially available from G. E. Silicones); Dow Corning 244, Dow Corning 245, Dow Corning 246, Dow Corning 344, and Dow Corning 345, (commercially available from Dow Corning Corp.); Silicone Fluids SWS-03314, SWS-03400, F-222, F-223, F-250, and F-251 (commercially available from SWS Silicones Corp.); Volatile Silicones 7158, 7207, 7349 (available from Union Carbide); Masil SF-V (available from Mazer); and combinations thereof.

Other suitable carriers for use in the compositions include nonvolatile silicone emollients, preferably low viscosity nonvolatile silicone carriers having a viscosity of less than about 500 cs, more preferably from about 5 cs to about 50 cs, more preferably from about 5 cs to about 20 cs. These silicone emollients include, but are not limited to, polyalkylsiloxanes, polyalkyarylsiloxanes and polyethersiloxane copolymers. Examples of such emollients are well known in the art, some of which are described in 1 *Cosmetics, Science and Technology* 27–104 (M. Balsam and E. Sagarin ed. 1972); U.S. Pat. No. 4,202,879, issued to Shelton on May 13, 1980; and U.S. Pat. No. 5,069,897, issued to Orr on Dec. 3, 1991; which descriptions are incorporated herein by reference.

Organic carriers for use in the compositions include saturated or unsaturated, substituted or unsubstituted, branched or linear or cyclic, organic compounds that are also liquid under ambient conditions. These carriers include hydrocarbon oils, alcohols, organic esters and ethers that are liquid under ambient conditions. Preferred organic carriers include mineral oil and other hydrocarbon oils, some examples of which are described in U.S. Pat. No. 5,019,375, issued to Tanner et al. on May 28, 1991, which description is incorporated herein by reference. Other suitable organic liquid carriers include Permethyl 99A, Permethyl 101A, Permethyl 102A, (Permethyl available from Permethyl Corp.), Isopar M, Isopar C, Isopar E, Isopar G, Isopar L, Isopar H, Isopar V (Isopar available from Exxon), isohexadecane, diisopropyl adipate, butyl stearate, isododecane, light mineral oil, petrolatum and other similar materials.

Optional Components

The anhydrous antiperspirant cream compositions of the present invention may further comprise one or more optional components which may modify the physical or chemical characteristics of the compositions or serve as additional "active" components when deposited on the skin. The compositions may also further comprise optional inert ingredients. Many such optional materials are known in the antiperspirant art and may be used in the antiperspirant compositions herein, provided that such optional materials are compatible with the essential materials described herein, or do not otherwise unduly impair product performance.

Nonlimiting examples of optional materials include components such as colorants, emulsifiers, chelants, distributing agents, preservatives, residue masking agents, and wash-off aids. Examples of such optional materials are described in U.S. Pat. No. 4,049,792, Elsnau, issued Sep. 20, 1977; Canadian Patent 1,164,347, Beckmeyer et al., issued Mar. 27, 1984; U.S. Pat. No. 5,019,375, Tanner et al., issued May 28, 1991; and U.S. Pat. No. 5,429,816, Hofrichter et al., issued July 4, 1995; which descriptions are incorporated by reference herein.

Packaged Composition

The anhydrous antiperspirant cream compositions of the present invention preferably further comprise a packaged delivery system. Examples of packaged delivery systems for antiperspirant cream products are well known in the art, and typically comprise an enclosed package or container having an interior chamber, a dispensing end, and an attached perforated dome or other perforated surface.

The anhydrous antiperspirant cream compositions are particularly effective when combined with a dispensing package containing a perforated dome. The perforated dome has a plurality of openings, apertures, or orifices through which the perfume/cyclodextrin complexes and other essential ingredients of the composition can easily flow. The ease of extrusion of the composition through the perforated dome helps to maintain the integrity of the cyclodextrin complex particles for sustained release of the encapsulated perfume materials. The perforated dome also helps provide uniform spreading of the composition to the axillary area or other areas of the skin, which results in improved antiperspirant and odor control. Moreover, the compositions of the present invention exhibit minimal or no solvent syneresis during extrusion through a perforated dome.

The perforated dome of the dispensing package of the present invention has a convex surface, preferably a ridged surface, having a plurality of apertures extending through the thickness of the dome, and through which the antiperspirant cream composition is extruded and flows to the intended side of application on the skin. The perforated dome is attached or fixed to the dispensing end of the container body, and has a convex configuration that extends away or protrudes from the container body. The thickness of the perforated dome is preferably from about 0.25 mm to about 1.53 mm, more preferably from about 0.7 mm to about 0.97 mm.

The apertures in the perforated dome represent from about 15% to about 80%, preferably from about 30% to about 60%, more preferably from about 39% to about 50%, of the surface area of the perforated dome. The average aperture area of the perforated dome is preferably from about 0.12 $cm^2$ to about 0.50 $cm^2$, more preferably from about 0.2 $cm^2$ to about 0.35 $cm^2$, wherein the apertures areas can have a circular or noncircular configuration, preferably a circular configuration having an average circular diameter preferably from about 1.9 mm to about 2.6 mm, more preferably from about 0.6 mm to about 26 mm. The circular configuration of the apertures provide for improved flow of the antiperspirant cream through the perforated dome, and furthermore provides for extrusion of the perfume/cyclodextrin complex without impairment of the complex particle which can lead to premature release of the perfume materials.

In particular, the packaged anhydrous antiperspirant cream compositions of the present invention comprise any of the antiperspirant cream compositions described hereinbefore, but preferably comprise from about 0.5% to about 35% by weight of a particulate antiperspirant active; from about 0.1% to about 20% by weight of a suspending or thickening agent; from about 10% to about 90% by weight of an anhydrous liquid carrier wherein the anhydrous liquid carrier has a solubility parameter of from about 3 $(cal/cm^3)^{0.5}$ to about 13 $(cal/cm^3)^{0.5}$; from about 0.05% to about 20% by weight perfume/cyclodextrin inclusion complex; and a perforated dome which provides for extrusion of the composition from the package without impairment of the perfume/cyclodextrin complex; wherein the antiperspirant cream composition has a penetration force value of from about 75 gram·force to about 500 gram·force.

Examples of suitable perforated domes for use in the packaged compositions of the present invention include those known in the art for application of creams, or those that are otherwise effective for delivering the compositions of the present invention to the skin. Some examples of such perforated domes, and some dispensing packages for use with compositions herein, are described in U.S. Pat. No. 5,000,356, issued to Johnson et al. on Mar. 19, 1991; and U.S. patent application Ser. No. 09/054,091, filed Apr. 2, 1998; which descriptions are incorporated by reference herein.

Method of Manufacture

The anhydrous antiperspirant cream compositions of the present invention may be prepared by any known or otherwise effective technique, suitable for providing an antiperspirant cream composition provided that the perfume/cyclodextrin complex component of the composition is incorporated into the composition in the manner described herein. Such methods involve formulation of the essential components of the composition to form a soft cream wherein the final antiperspirant cream product has increased capacity to contact the axillary area or other areas of the skin.

Methods for preparing the anhydrous antiperspirant cream compositions of the present invention include those methods well known in the art for formulating compositions containing small suspending or thickening agent particles. Such methods include the use of nucleating agents, formulation with select carriers or suspending or thickening agents or carrier/suspending or thickening agent combinations, controlling formulation and processing temperatures, and so forth.

A preferred method for preparing such a composition comprises a formulation step followed by a controlled solidification step. The formulation step involves 1) combining the following ingredients: from about 0.5% to about 35% by weight of a particulate antiperspirant active; from about 0.1% to about 20% by weight of a suspending or thickening agent; and from about 10% to about 90% by weight of an anhydrous liquid carrier wherein the anhydrous liquid carrier has a solubility parameter of from about 3 $(cal/cm^3)^{0.5}$ to about 13 $(cal/cm^3)^{0.5}$. The process preferably involves thorough mixing to of the essential components described in step 1, and optional components, at the desired temperature while adding minimal amounts of heat or other energy to liquefy and thoroughly mix all of the added ingredients. Processing temperatures will generally range from about 28° C. to about 125° C., more preferably from about 35° C. to about 100° C., even more preferably from about 50° C. to about 90° C., but will vary with the melt profile of the ingredients in the mixture. In this context, the term "liquefy" means that the substantially all of the suspending or thickening agent and carrier material in the composition are melted or are otherwise in the form of a combined flowable liquid, which combined flowable liquid comprises particulate antiperspirant active substantially uniformly dispersed therethrough. The perfume/cyclodextrin complex and optional free perfume materials are added to the composition after liquefying the essential and other optional ingredients.

The second essential step in the preferred method of making the compositions involves solidification of the liquefied mixture described hereinabove. The solidification preferably involves removal of the composition from any added heat or other energy source, and/or by subjecting the liquefied composition to active cooling. It is essential, however, that once the solidification process begins, that the liquefied composition is allowed to solidify to the requisite hardness without the addition of substantial amounts of shear force, preferably without the addition of any additional shear force.

The preferred method may further comprise the addition of optional materials to the composition. Such addition is preferably during the formulation step, wherein the essential and optional ingredients (excluding the optional free perfumes) are mixed together to form a liquefied admixture. In making the compositions of the present invention, care must be taken to assure that the particulate antiperspirant materials and perfume/cyclodextrin complex are dispersed relatively uniformly throughout the composition.

It has been found that the incorporation of the perfume/cyclodextrin complex into the composition improves perfume longevity, and provides sustained release of the perfume. The inclusion of perfume/cyclodextrin complexes in the anhydrous antiperspirant cream compositions of the present invention provides extended contact between the complexes and human skin which results in perfume odor impressions for extended periods after application and during use of the antiperspirant cream product.

Method of Use

The anhydrous antiperspirant cream compositions of the present invention may be packaged in any antiperspirant cream containers known in the art, or other container suitable for topical delivery of a cream to the skin. These packaged compositions may then be applied topically to the skin by any conventional, known or otherwise effective means of topical application. Such methods preferably involve application of an effective amount of the anhydrous antiperspirant cream composition to the axilla or other area of the skin, preferably from about 0.1 gram to about 20 grams, more preferably from about 0.1 gram to about 10 grams, even more preferably from about 0.1 gram to about 1 gram, of the composition to the desired area of the skin. The applied cream is preferably rubbed over the applied surface using an applicator device or dispensing package having a perforated dome as described herein, and more preferably such rubbing action is continued until there is little or no visible residue on the applied surface.

These application methods are preferably applied to the desired areas, typically to the axilla or other area of the skin, one to two times daily, preferably once daily, to achieve effective antiperspirant and odor control over an extended period.

A preferred method of using the anhydrous antiperspirant compositions of the present invention comprises applying the composition topically through a dispensing package having a perforated dome as described hereinbefore, and which delivers the anhydrous antiperspirant cream composition of the present invention to the surface of the skin by extrusion through the perforated dome without impairment of the perfume/cyclodextrin complex.

The anhydrous antiperspirant cream compositions of the present invention may also be used in a conventional or otherwise effective manner to treat or prevent perspiration on areas of the human body, such as the axillary areas, which are prone to perspiration wetness. Specifically, an effective amount of any of the compositions described herein is applied topically to such areas one or more times a day. When this is done, the compositions provide effective antiperspirant performance, reduced residue on the skin, good dry skin feel, is easy to wash off, and improved fragrance longevity.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Examples I–VI

The following Examples I–VI describe perfume/cyclodextrin complexes of the present invention. Examples I–V are prepared by complexing the perfume materials with beta-cyclodextrin. Example VI is prepared by complexing the perfume materials with gamma-cyclodextrin. The process of preparing the complexes include mixing cyclodextrin and water in a round bottom flask, and heating the mixture to about 65° C. Mixing is continued while the perfume is slowly added, and a slurry is usually observed at this point. The mixture is then removed from heat, and stirring is continued until the mixture cools to ambient temperature. The resultant slurry is now a creamy precipitate in appearance, and this is an indication that a complex has formed. The complex is then dried in a convection oven at a temperature of from about 100° C. or lower. The complex can be washed prior to drying to remove any uncomplexed perfume materials. The resultant complexes are incorporated into the anhydrous antiperspirant cream compositions of the present invention, and provide sustained release of the perfume materials until the complex comes in contact with human body fluid such as sweat.

Perfume/Cyclodextrin Complexes

| Component: | Example I | Example II | Example III |
|---|---|---|---|
| Alpha damascone | 0.12 | 0.08 | 0.16 |
| Amyl acetate | 0.89 | 0.18 | — |
| Amyl salicylate | — | 1.39 | 3.83 |
| Base jasmin AN101970 | 21.56 | 15.76 | 21.88 |
| Benzaldehyde | 0.11 | 0.16 | 0.10 |
| Benzyl acetate | 4.25 | 6.14 | 5.11 |
| Benzyl alcohol | — | — | 5.23 |
| Benzyl propionate | 0.75 | 0.36 | 0.65 |
| Celery seed oil | 0.03 | 0.01 | — |
| Cis-3-hexenyl salicylate | 8.95 | 1.62 | 3.52 |
| Citronellol | 1.76 | 1.44 | 1.84 |
| Cyfleural S6MC | — | 2.42 | — |
| Cymal | 2.28 | 0.05 | 0.55 |
| Beta-damascone | 0.12 | 0.08 | 0.10 |
| Decyl aldehyde | 0.14 | 0.08 | 0.09 |
| Dimethyl benzyl carbinyl acetate | 0.30 | 0.02 | 0.72 |
| Dihydro-nor-cyclopentadienyl acetate | 2.54 | 0.56 | 1.53 |
| Dihydro-nor-cyclopentadienyl propionate | — | 0.17 | 0.88 |
| Geraniol | 3.11 | 3.24 | 1.94 |
| Geranium S | 0.29 | 0.33 | 0.12 |
| Helional | 1.21 | 2.02 | 0.77 |
| Gamma methyl ionone | 3.53 | 7.21 | 4.26 |
| Kir base #9741 (BBA) | — | 1.21 | 0.51 |
| Lemon C.P. | 1.58 | 0.56 | 1.08 |
| Ligustral | 0.08 | 0.17 | 0.03 |
| Linalool | 2.31 | — | — |
| Lyral | 6.52 | 5.36 | — |
| Methyl dihydro jasmonate | 7.08 | 8.65 | 2.65 |
| Methyl phenyl carbinyl acetate | 0.73 | 0.16 | 0.58 |
| Orange oil, cold pressed | 1.66 | 0.57 | — |
| 2-methyl-3-(para tert butylphenyl)-propionaldehyde | 2.30 | 7.03 | 5.71 |
| Phenyl acetaldehyde 40% in PEA | 0.01 | 0.01 | 0.03 |
| Phenyl ethyl alcohol | 4.63 | 8.47 | 3.25 |
| Terpineol | 4.24 | 2.43 | 3.71 |
| Tetra-hydro linalool | 4.02 | 2.02 | 4.35 |
| Undecalactone | 0.43 | 0.56 | 0.39 |
| Undecylenic aldehyde | 0.17 | 0.08 | 0.10 |
| VL Base PG | 12.30 | 19.40 | 24.33 |

Perfume/Cyclodextrin Complexes

| Component: | Example IV | Example V | Example VI |
|---|---|---|---|
| Alpha damascone | 0.22 | 0.02 | 0.22 |
| Amyl acetate | 3.03 | 0.12 | 3.03 |
| Amyl salicylate | — | 5.34 | — |
| Base jasmin AN101970 | — | 13.76 | — |
| Benzaldehyde | 0.25 | 0.16 | 0.25 |
| Benzyl acetate | 9.31 | 7.23 | 9.31 |
| Benzyl alcohol | 4.25 | — | 12.78 |
| Benzyl propionate | 2.62 | 0.52 | 2.62 |
| Celery seed oil | — | 0.01 | — |
| Citronellol | 5.76 | 2.55 | 5.76 |
| Cyfleural S6MC | — | 3.46 | — |
| Cymal | — | 0.32 | — |
| Beta-damascone | 0.13 | 0.12 | 0.13 |
| Decyl aldehyde | 0.38 | 0.05 | 0.38 |
| Diethyl phthalate | 2.86 | — | — |
| Dimethyl benzyl carbinyl acetate | 3.31 | 0.12 | 3.31 |
| Dimethyl benzyl carbinol | 1.20 | — | 1.20 |
| Dihydro-nor-cyclopentadienyl acetate | — | 0.76 | — |
| Dihydro-nor-cyclopentadienyl propionate | — | 0.43 | — |
| Geraniol | 6.65 | 5.44 | 6.65 |
| Geranyl acetate | 2.62 | — | 2.62 |
| Geranium S | — | 0.52 | — |
| Helional | 3.36 | — | 3.36 |
| Gamma methyl ionone | — | 6.55 | — |
| Kir base #9741 (BBA) | — | 1.78 | — |
| Lemon C.P. | 4.50 | 0.88 | 4.50 |
| d-limonene | 4.78 | — | 4.78 |
| Ligustral | — | 0.15 | — |
| Linalool | 11.56 | — | 11.56 |
| Lyral | — | 2.31 | — |
| Methyl dihydro jasmonate | — | 10.36 | — |
| Methyl phenyl carbinyl acetate | 0.78 | 0.28 | 0.78 |
| Orange oil, cold pressed | 1.44 | 0.75 | 1.44 |
| 2-methyl-3-(para tert butylphenyl)-propionaldehyde | — | 8.25 | — |
| Phenyl acetaldehyde 40% in PEA | 0.17 | 0.05 | 0.17 |
| Phenyl ethyl acetate | 2.93 | — | 2.93 |
| Phenyl ethyl alcohol | 11.62 | 7.63 | 11.62 |
| Terpineol | 3.66 | 2.99 | 3.66 |
| Tetra-hydro linalool | 5.86 | 7.32 | 5.86 |
| Triethyl citrate | 5.67 | — | — |
| Undecalactone | 0.61 | 0.63 | 0.61 |
| Undecylenic aldehyde | 0.47 | 0.13 | 0.47 |
| VL Base PG | — | 9.01 | — |

Examples VII–XII

The following Examples VII–XII describe anhydrous antiperspirant cream compositions of the present invention. Each of the exemplified compositions are prepared by combining all of the listed components, except the perfume/cyclodextrin complex and optional free perfumes, and heating the combination to 100° C. with agitation to form a hot liquid. The perfume/cyclodextrin complex and optional free perfumes are then added to the hot liquid. The heated liquid is allowed to cool with agitation until just before the point of solidification, at which point the cooled, liquid composition is filled into jars or cream applicators and allowed to cool without further agitation or other applied shear to form a stiff cream within the corresponding applicator package. Each packaged composition is then fitted with the perforated dome as defined herein, through which the composition may be extruded and applied topically to the skin.

| Anhydrous Antiperspirant Cream Compositions | | | | | | |
|---|---|---|---|---|---|---|
| Component | Example VII | Example VIII | Example IX | Example X | Example XI | Example XII |
| Al Zr trichlorohydrex glycinate[1] | 26.00 | 25.25 | 25.25 | 26.00 | 25.25 | 25.25 |
| Cyclopentasiloxane SF1202[2] | 66.00 | 58.81 | 62.21 | 58.09 | 62.98 | 58.25 |
| Dimethicone (10 cs) | — | 5.00 | 5.00 | 5.00 | 5.00 | 5.00 |
| Glyceryl tribehanate | — | 5.00 | 5.00 | 5.00 | 3.25 | 5.00 |
| C18–C36 triglyceride combination[3] | — | 1.25 | 1.25 | — | 0.80 | 1.25 |
| C20–C40 alcohols[4] | 5.00 | — | — | — | — | — |
| Perfume/CD Complex (Example I) | 2.50 | — | — | — | — | — |
| Perfume/CD Complex (Example II) | — | 3.94 | — | — | — | 4.50 |
| Perfume/CD Complex (Example III) | — | — | 0.79 | — | — | — |
| Perfume/CD Complex (Example IV) | — | — | — | 5.91 | — | — |
| Perfume/CD Complex (Example V) | — | — | — | — | 1.97 | — |
| Free Perfume | 0.50 | 0.75 | 0.50 | — | 0.75 | 0.75 |

[1]Supplied by Westwood Chemical Corporation
[2]Supplied by G. E. Silicones
[3]Syncrowax HGL-C from Croda
[4]Unilin 425 from Petrolite

What is claimed is:

1. An anhydrous antiperspirant cream composition comprising:
   (a) antiperspirant active;
   (b) a perfume/cyclodextrin inclusion complex; and
   (c) from about 10% to about 90% by weight of an anhydrous liquid carrier;
   wherein the composition has a penetration force value of from about 75 gram·force to about 500 gram·force, and contains less than about 2% by weight of free or added water.

2. The composition of claim 1 wherein the composition comprises from about 0.5% to about 35% by weight of the antiperspirant active.

3. The composition of claim 2 wherein the composition comprises from about 0.05% to about 20% by weight of the perfume/cyclodextrin inclusion complex.

4. The composition of claim 3 wherein the perfume is selected from the group consisting of anethole, benzaldehyde, decyl aldehyde, amyl acetate, benzyl acetate, benzyl alcohol, benzyl formate, benzyl propionate, isobornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, helional, cis-3-hexenol, cis-3-hexenyl acetate, dipropylene glycol, diethyl phthalate, phenyl ethyl acetate, dihydrocitronellal, d-limonene, linalool, linalool oxide, tetra-hydro linalool, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, prenyl acetate, manjantol, ambrettolide, ambroxan, cetelox, phenyl ethyl alcohol, phenyl acetaldehyde, alpha-pinene, beta-pinene, gamma-terpinene, alpha-terpineol, beta-terpineol, terpinyl acetate, vertenex (para-tertiary-butyl cyclohexyl acetate), alpha damascone, damascone beta, undecalactone, undecylenic aldehyde, amyl cinnamic aldehyde, iso-amyl salicylate, beta-caryophyllene, cedrene, cinnamic alcohol, coumarin, cymal, dimethyl benzyl carbinyl acetate, dimethyl benzyl carbinol, ethyl vanillin, eugenol, iso-eugenol, dihydro-nor-cyclopentadienyl acetate, dihydro-nor-cyclopentadienyl propionate, heliotropine, cyclohexyl salicylate, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, veratraldehyde, 2-methyl-3-(para tert butylphenyl)-propionaldehyde, benzophenone, benzyl salicylate, ethylene brassylate, galaxolide (1,3,4,6,7,8-Hexahydro-4,6,6,7,8,8-hexamethyl-cyclopenta-gamma-2-benzopyran), hexyl cinnamic aldehyde, lyral (4-(4-hydroxy-4-methyl pentyl)-3-cyclohexene-10-carboxaldehyde), methyl cedrylone, dihydro isojasmonate, methyl dihydro jasmonate, methyl-beta-naphthyl ketone, gamma decalactone, musk indanone, musk ketone, musk tibetene, phenylethyl phenyl acetate, cyfleural S6MC, PE isobutyrate, PE propionate, tripal, LRG 201, ligustral, natural oils, and mixtures thereof.

5. The composition of claim 4 wherein the cyclodextrin is selected from the group consisting of alpha-cyclodextrins, beta-cyclodextrins, gamma-cyclodextrins, derivatives thereof, and mixtures thereof.

6. The composition of claim 1 further comprising from about 0.10% to about 10% by weight of free perfume.

7. The composition of claim 6 wherein the anhydrous liquid carrier is selected from the group consisting of volatile silicones, nonvolatile silicones, mineral oil, hydrocarbon oils, isohexadecane, diisopropyl adipate, butyl stearate, isododecane, light mineral oil, pertrolatum, and mixtures thereof.

8. The composition of claim 7 wherein the anhydrous liquid carrier is a combination of a volatile silicone and a nonvolatile silicone.

9. The composition of claim 7 further comprising from about 0.1% to about 20% by weight of a suspending or thickening agent selected from the group consisting of fatty alcohols, fatty alcohol esters, fatty acids, fatty acid amides, fatty acid esters, fatty acid ethers, ethoxylated fatty alcohols, ethoxylated fatty acids, corresponding salts thereof, and mixtures thereof.

10. The composition of claim 9 wherein the fatty acid ester comprises glyceryl tribehanate and other triglycerides, wherein at least about 75% of the fatty acid ester moieties of said other triglycerides have from about 18 to about 36 carbon atoms, and the molar ratio of glyceryl tribehanate to said other triglycerides is from about 20:1 to about 1:1.

11. A packaged anhydrous antiperspirant cream composition comprising:
   (a) antiperspirant active;
   (b) a perfume/cyclodextrin inclusion complex; and (c) a dispensing package containing the composition, wherein the dispensing package comprises
  i) a container body having an interior chamber and dispensing end; and
  ii) a perforated dome attached to the dispensing end of the container body and having a plurality of openings extending through the thickness of the perforated dome and covering from about 15% to about 80% of the total surface area of the perforated dome.

12. The composition of claim 11 wherein the composition comprises from about 0.5% to about 35% by weight of the antiperspirant active.

13. The composition of claim 12 wherein the composition comprises from about 0.05% to about 20% by weight of the perfume/cyclodextrin inclusion complex.

14. The composition of claim 13 wherein the perfume is selected from the group consisting of anethole, benzaldehyde, decyl aldehyde, amyl acetate, benzyl acetate, benzyl alcohol, benzyl formate, benzyl propionate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, helional, cis-3-hexenol, cis-3-hexenyl acetate, dipropylene glycol, diethyl phthalate, phenyl ethyl acetate, dihydrocitronellal, d-limonene, linalool, linalool oxide, tetra-hydro linalool, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, prenyl acetate, manjantol, ambrettolide, ambroxan, cetelox, phenyl ethyl alcohol, phenyl acetaldehyde, alpha-pinene, beta-pinene, gamma-terpinene, alpha-terpineol, beta-terpineol, terpinyl acetate, vertenex (para-tertiary-butyl cyclohexyl acetate), alpha damascone, damascone beta, undecalactone, undecylenic aldehyde, amyl cinnamic aldehyde, iso-amyl salicylate, beta-caryophyllene, cedrene, cinnamic alcohol, coumarin, cymal, dimethyl benzyl carbinyl acetate, dimethyl benzyl carbinol, ethyl vanillin, eugenol, iso-eugenol, dihydro-nor-cyclopentadienyl acetate, dihydro-nor-cyclopentadienyl propionate, heliotropine, cyclohexyl salicylate, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, veratraldehyde, 2-methyl-3-(para tert butylphenyl)-propionaldehyde, benzophenone, benzyl salicylate, ethylene brassylate, galaxolide (1,3,4,6,7,8-Hexahydro-4,6,6,7,8,8-hexamethyl-cyclopenta-gamma-2-benzopyran), hexyl cinnamic aldehyde, lyral (4-(4-hydroxy-4-methyl pentyl)-3-cyclohexene-10-carboxaldehyde), methyl cedrylone, dihydro isojasmonate, methyl dihydro jasmonate, methyl-beta-naphthyl ketone, gamma decalactone, musk indanone, musk ketone, musk tibetene, phenylethyl phenyl acetate, cyfleural S6MC, PE isobutyrate, PE propionate, tripal, LRG 201, ligustral, natural oils, and mixtures thereof.

15. The composition of claim 13 wherein the cyclodextrin is selected from the group consisting of alpha-cyclodextrins, beta-cyclodextrins, gamma-cyclodextrins, derivatives thereof, and mixtures thereof.

16. The composition of claim 11 further comprising from about 0.10% to about 10% by weight of free perfume.

17. The composition of claim 16 further comprising from about 10% to about 90% by weight of an anhydrous liquid carrier selected from the group consisting of volatile silicones, nonvolatile silicones, mineral oil, hydrocarbon oils, isohexadecane, diisopropyl adipate, butyl stearate, isododecane, light mineral oil, pertrolatum, and mixtures thereof.

18. The composition of claim 17 wherein the anhydrous liquid carrier is a combination of a volatile silicone and a nonvolatile silicone.

19. The composition of claim 17 further comprising from about 0.1% to about 20% by weight of a suspending or thickening agent selected from the group consisting of fatty alcohols, fatty alcohol esters, fatty acids, fatty acid amides, fatty acid esters, fatty acid ethers, ethoxylated fatty alcohols, ethoxylated fatty acids, corresponding salts thereof, and mixtures thereof.

20. The composition of claim 19 wherein the fatty acid ester comprises glyceryl tribehenate and other triglycerides, wherein at least about 75% of the fatty acid ester moieties of said other triglycerides have from about 18 to about 36 carbon atoms, and the molar ratio of glyceryl tribehenate to said other triglycerides is from about 20:1 to about 1:1.

21. An anhydrous antiperspirant cream composition comprising:
  (a) antiperspirant active;
  (b) a perfume/cyclodextrin inclusion complex wherein the complex comprises a highly volatile perfume having a boiling point less than or equal to 250° C.; and
  (c) from about 10% to about 90% by weight of an anhydrous liquid carrier;
wherein the composition has a penetration force value of from about 75 gram·force to about 500 gram·force and contains less than about 2% by weight of free or added water.

22. The composition of claim 21 wherein the composition comprises from about 0.5% to about 35% by weight of the antiperspirant active.

23. The composition of claim 22 wherein the composition comprises from about 0.05% to about 20% by weight of the perfume/cyclodextrin inclusion complex.

24. The composition of claim 23 wherein the complex is substantially free of perfume materials having a boiling point of greater than 250° C.

25. The composition of claim 24 wherein the highly volatile perfume is selected from the group consisting of anethole, benzaldehyde, decyl aldehyde, benzyl acetate, benzyl alcohol, benzyl formate, benzyl propionate, iso-bomyl acetate, camphene, cis-citral (neral), citronellal, citronellol, citronellyl acetate, paracymene, decanal, dihydrolinalool, dihydromyrcenol, methyl benzyl carbinyl acetate, dimethyl benzyl carbinyl acetate, dimethyl phenyl carbinol, eucalyptol, helional, geranial, geraniol, geranyl acetate, geranyl nitrile, cis-3-hexenyl acetate, dihydrocitronellal, d-limonene, linalool, linalool oxide, tetra-hydro linalool, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, phenyl acetaldehyde, alpha-pinene, beta-pinene, gamma-terpinene, terpineol, alpha-terpineol, beta-terpineol, terpinyl acetate, vertenex (para-tertiarybutyl cyclohexyl acetate), gamma-methyl ionone, undecalactone, undecylenic aldehyde, alpha-damascone, beta-damascone, amyl acetate, lemon oil, orange oil, and mixtures thereof.

26. The composition of claim 24 wherein the cyclodextrin is selected from the group consisting of alpha-cyclodextrins, beta-cyclodextrins, gamma-cyclodextrins, derivatives thereof, and mixtures thereof.

27. The composition of claim 21 further comprising from about 0.10% to about 10% by weight of free perfume.

28. The composition of claim 27 wherein the anhydrous liquid carrier is selected from the group consisting of volatile silicones, nonvolatile silicones, mineral oil, hydrocarbon oils, isohexadecane, diisopropyl adipate, butyl stearate, isododecane, light mineral oil, pertrolatum, and mixtures thereof.

29. The composition of claim 28 wherein the anhydrous liquid carrier is a combination of a volatile silicone and a nonvolatile silicone.

30. The composition of claim 28 further comprising from about 0.1% to about 20% by weight of a suspending or thickening agent selected from the group consisting of fatty alcohols, fatty alcohol esters, fatty acids, fatty acid amides, fatty acid esters, fatty acid ethers, ethoxylated fatty alcohols, ethoxylated fatty acids, corresponding salts thereof, and mixtures thereof.

31. The composition of claim 30 wherein the fatty acid ester comprises glyceryl tribehenate and other triglycerides, wherein at least about 75% of the fatty acid ester moieties of said other triglycerides have from about 18 to about 36 carbon atoms, and the molar ratio of glyceryl tribehenate to said other triglycerides is from about 20:1 to about 1:1.

32. A method for treating and preventing perspiration in humans, which method comprises applying from about 0.1 gram to about 20 grams of the composition of claim 1 to the skin.

33. A method for treating and preventing perspiration in humans, which method comprises applying from about 0.1 gram to about 20 grams of the composition of claim 11 to the skin.

34. A method for treating and preventing perspiration in humans, which method comprises applying from about 0.1 gram to about 20 grams of the composition of claim 21 to the skin.

* * * * *